United States Patent [19]
Benkeser et al.

[11] Patent Number: 4,533,752
[45] Date of Patent: Aug. 6, 1985

[54] PROCESS FOR REDUCING AROMATIC COMPOUNDS IN ETHYLENEDIAMINE WITH CALCIUM

[75] Inventors: Robert A. Benkeser, West Lafayette, Ind.; James A. Laugal, Lostant, Ill.; Angela Rappa, Baltimore, Md.

[73] Assignee: Purdue Research Foundation, West Lafayette, Ind.

[21] Appl. No.: 643,442

[22] Filed: Aug. 23, 1984

[51] Int. Cl.³ .............................................. C07C 5/10
[52] U.S. Cl. .................................... 564/428; 564/450; 568/667; 568/734; 568/743; 568/823; 585/266; 585/271; 585/267
[58] Field of Search ............... 585/266, 267, 268, 271, 585/272; 564/428, 450; 568/667, 734, 743, 823

[56] References Cited

U.S. PATENT DOCUMENTS 3,278,618 10/1966 Amagasa et al. ................. 585/267

FOREIGN PATENT DOCUMENTS 40-3731927 4/1965 Japan .................................. 585/267
40-48724 8/1965 Japan .................................. 585/267
41-1025426 4/1966 United Kingdom ............... 585/267

OTHER PUBLICATIONS

Benkeser et al., J. Org. Chem., 44, 3737–3739, (1979).
Benkeser et al., J. Org. Chem., 48, 2796–2802, (1983).
Benkeser et al., Synth. Commun. 13, 1103–1116, (1983).
Benkeser et al., Tetrahedron Lett., 25, 2089–2092, (1984).

Primary Examiner—D. E. Gantz
Assistant Examiner—A. Pal
Attorney, Agent, or Firm—Barnes & Thornburg

[57] ABSTRACT

Olefins are produced by containing an organic compound having at least one benzene ring with ethylenediamine and calcium metal, the calcium metal being used in large excess or alternatively in conjunction with an inert abrasive particulate substance. Substantially all of the organic compounds are converted to corresponding cyclic olefins, largely mono-olefins.

18 Claims, No Drawings

PROCESS FOR REDUCING AROMATIC COMPOUNDS IN ETHYLENEDIAMINE WITH CALCIUM

The Government has rights in this invention pursuant to Contract No. DE-AC02-81ER10989 awarded by the Department of Energy.

BACKGROUND OF THE INVENTION

1. Field of the Invention

This invention is concerned with the manufacture of cyclic olefinic compounds. It is particularly concerned with the reduction of organic compounds having at least one benzene ring to olefins of similar cyclic structures, largely mono-olefins, in a calcium-ethylenediamine system.

2. Description of the Prior Art

The Birch reduction process is a well known method that has been used for a number of years to reduce aromatic hydrocarbons to diolefinic hydrocarbons. In the Birch reduction process, aromatic hydrocarbons are reduced by means of metallic sodium or lithium in liquid ammonia, in the presence of an alcohol. Sodium is very reactive and requires a great deal of caution in use and handling. Likewise, liquid ammonia has a very low boiling point and is therefore difficult to handle. It is obviously desirable to provide a safer and easier reduction process.

A lithium-amine system for reducing simple aromatic hydrocarbons to cyclic alkenes has been reported by Benkeser et al, J. Am. Chem. Soc., 77, 3230, 1955.

The reduction of aromatic compounds with calcium, ammonia, and ether has been reported by Dumanskii et al, J. Russ. Phys. Chem. Soc., 48, 994, (1916), Kazanskii et al, J. Gen. Chem. USSR, 8, 642 (1938), and Campbell et al, J. Am. Chem. Soc., 67, 282 (1945). The procedures reported by these workers are cumbersome and usually give products that are quite impure and difficult to separate. As a result, calcium reductions have never gained widespread acceptance and have been used only sporadically through the years.

The production of monoolefins from aromatic hydrocarbons in a reducing system utilizing calcium metal in a mixture of methylamine and ethylenediamine has been described by Benkeser et al, Org. Chem., 44, 3737 (Oct. 12, 1979). The reduction process was carried out at 0° C. using calcium metal in an amount only slightly in excess of the stoichiometric quantity necessary to effect the reduction. When ethylenediamine was used alone as solvent with 25% excess calcium to reduce isopropylbenzene, a very low conversion resulted and 64% of the unreacted isopropylbenzene was recovered.

Filed of even date herewith, is a patent application, serial number 643,649, by the same inventors disclosing the reduction of organic compounds having at least one benzene ring to polyolefins in a calcium-amine-alcohol system, the calcium metal being used in large excess or alternatively in conjunction with an inert abrasive particulate substance. Unlike the invention described in the present application, the reduction in the copending application is carried out in the presence of alcohol, and polyolefins are produced having at least two double bonds. As will be seen below, other methods and operating conditions are employed in the invention of the present application. Moreover, the reaction products of the present invention are largely mono-olefins, diolefins being produced only under limited conditions.

BRIEF SUMMARY OF THE INVENTION

It has now been discovered that organic compounds having at least one benzene ring can be reduced largely to olefins of corresponding cyclic structure in high yield by contacting such organic compounds with ethylenediamine and an excess of calcium metal, optionally in the presence of an inert abrasive particulate substance. The calcium metal is suitably used in a proportion to the organic compound at least 100% in excess of the stoichiometric quantity necessary for complete reduction of the organic compound, but can be used in smaller excess (e.g., down to around 10%) provided the said particulate substance is also used. The function of the particulate substance is to remove the calcium amides from the surface of the calcium by abrasive action, with the result that the calcium metal is not deactivated by masking as in the prior art methods but fresh active calcium is continuously presented to the reaction mixture. As will be seen hereafter, the calcium-ethylenediamine system is much more effective for the formation of olefins, largely mono-olefins, than prior art reduction systems.

The process of this invention, more fully described hereafter, is effective in many cases to convert substantially all of the organic compounds having at least one benzene ring to corresponding cyclic olefins having the same structure as such organic compounds except for degree of unsaturation. Depending on the starting material, cyclic monoolefins or cyclic diolefins are produced. The resulting olefin is a cyclic olefin having at least one double bond and in special cases, having a second double bond when the benzene ring bears a substituent or substituents hindering the said reaction.

DETAILED DESCRIPTION OF THE INVENTION

In the practice of this invention an organic compound is contacted with calcium metal and an alkylene polyamine solvent. A wide variety of organic compounds having a least one benzene ring can be used as the starting material in this invention. Representative organic compounds useful in the invention to produce cyclic mono-olefins are benzene, cumene, xylene, indan, biphenyl, fluorene, pseudocumene, benzyl cyanide, naphthalene, 2-naphthol, 1 methylnaphthalene, 2-methylnaphthalene, acenaphthene, acenaphthalene, 1,2 diphenylmethane, 1,2 diphenylethane, dibenzothiophene, 2 methoxynaphthalene, and other substituted benzenes and naphthalenes and the like, having fewer than four substituents on their central ring.

Organic compounds such as I naphthylamine and 1-naphthol have been reduced to the corresponding organic compounds 5,6,7,8 tetrahydro 1-naphthylamine and 5,6,7,8-tetrahydro 1 naphthol respectively.

Organic compounds having a substituent or substituents hindering the reduction of the benzene ring are reduced to diolefins of corresponding cyclic structure. Such hindered organic compounds include benzoic acid and the like.

Organic compounds having four substituents on their benzene ring (or on their cental ring where the hydrocarbon is a fused ring structure) are also reduced to corresponding cyclic diolefins. Such tetra-substituted organic compounds that can be reduced to cyclic diolefins in high conversions include durene, anthracene, 1,2,3,4-tetramethylbenzene and the like.

Representative alkylene polyamine solvents useful in the invention comprise one or more amine solvents such as ethylenediamine, diethylenetriamine, triethylenetetramine, tetramethylenediamine, 1,2,5-pentanetriamine, 1-methyltetramethylenediamine, hexamethylenetetramine, and the like. The alkylene polyamine solvent may also be supplemented with tetrahydrofuran (THF), diethyl ether, petroleum ether, or the like for the purpos of maximizing solubility of the organic compound starting material.

The calcium metal useful in this invention is preferably in the form of calcium turnings or calcium shot and preferably in the form of substantially pure calcium. Generally an excess of around 10% to around 25% calcium, when used or described herein, is sufficient to effect the desired reduction, based on the stoichiometric amounts necessary to effect complete reduction of the starting material.

In a preferred embodiment of the present invention, calcium metal is used in an amount greatly in excess of the stoichiometric quantity necessary to reduce the organic compound starting material to a corresponding cyclic olefin, the preferred exces of calcium being at least 100% of the stoichiometric amount. Calcium is relatively cheap and readily available. Thus this invention significantly reduces the problem of calcium masking arising from the formation of insoluble calcium alkylamides on the metal surface and represents a very economical alternative to the prior art calcium-amine mixture reducing systems.

In another embodiment of the present invention, calcium is maintained in active form by subjecting the reaction mixture to vigorous stirring (e.g. with a high-shear device such as a Hershberg stirrer or the like) in the presence of inert abrasive particulates whereby the insoluble coatings that tend to form on the surface of the calcium metal are removed by the abrasive action of the inert particles and fresh reactive calcium is continuously available for the reaction mixture. Suitable abrasive particulate materials include sand, silicon carbide, silica-alumina, diatomaceous earth, and the like. In this embodiment of the invention, the proportion of excess calcium can be substantially reduced, e.g. to as little as 10% over the stoichiometric amount.

The reduction step is carried out at a temperature ranging from about $-10°$ C. to about 100° C., preferably from about $-5°$ C. to about 50° C. A benefit of the present invention is that by utilizing a solvent such as ethylenediamine, the reduction reaction can be performed at ambient temperatures, around 20° C. to 30° C., representing a significant improvement over the prior art calcium-amine mixture and Birch-type reduction processes. The use of ambient or higher operational temperatures greatly facilitates manufacturing and handling procedures. For best selectivity in the reduction, temperatures around $-5°$ C. to $+5°$ C. can be used, but require the presence of additional solvent to maintain the polyalkylene polyamine in solution. In general, temperatures in the range of about $-0°$ C. to about 100° C. can be used in the invention.

The proportions of starting material to alkylene polyamine and supplemental solvent are not critical but should be chosen to produce a fluid reaction medium. In many cases, a supplemental solvent will not be necessary. In other cases, e.g., naphthalene, anthracene, and certain alkylene polyamines, the materials are normally solid and a sufficient quantity of supplemental solvent is needed to produce the desired fluid reaction medium.

In carrying out the process of the present invention, a reaction vessel is equipped with means for agitating the vessel contents and means for condensing solvent vapors in order to prevent their loss from the reaction vessel. Prior to the addition of any chemical reactants, the vessel is dried and may, if desired, be purged with an inert gas, such as nitrogen.

An organic compound starting material of the defined class, calcium metal, alkylene polyamine, and optional solvent are added to the reaction vessel and adjusted with stirring to the desired reaction temperature, after which stirring is continued until the reduction of the starting material to the desired olefinic product is substantially completed. Such a time period will generally range from about 1 hour to about 30 hours, most commonly from about 8 to about 10 hours. The reaction time will vary to some extent depending on the starting materials. In certain cases, the reaction may be sufficiently exothermic that exterior cooling may be necessary to control the temperature.

The reaction product mixture comprising reacted and unreacted starting material as well as unreacted calcium and calcium alkylamides is conveniently worked up by dissolving the calcium and calcium alkylamides in acid or aqueous ammonium chloride. Two layers are formed and separated and the olefinic products are recovered by distillation of the organic layer.

The invention described herein utilizes inexpensive compounds which are readily available to make more expensive compounds having commercial value. In addition, the process materials employed in the present invention are easier and safer to handle than the materials used in prior art.

The following examples illustrate the application of the present invention to a variety of starting materials.

EXAMPLES 1-11

In each of the following tests, an organic compound identified in Table 1 was placed in a reaction flask, together with calcium in the form of turnings or shot, and freshly distilled ethylenediamine. The flask was equipped with a mechanical stirrer, a gas inlet tube, and a reflux condenser through the jacket of which chilled water was circulated. The proportions of organic compound and calcium added to the reaction vessel are summarized in Table 1. With the exception of tetralin and p xylene, 75 ml of ethylenediamine were used in each example. For tetralin and p-xylene, 150 ml of ethylenediamine were used in the reaction.

The mixture was stirred for the amount of time indicated in Table 1. If the reaction became too vigorous, it was controlled with a cold water bath. Prolonged cooling was avoided, since the ethylenediamine tended to solidify at temperatures of about 9° C. and below, causing the reaction to stop.

TABLE 1

Reduction of Organic Compounds with Excess Calcium in Ethylenediamine

| Example No. | Organic Compound | mmol of Organic Compound | g-atom of Calcium | Reaction Time, hr | Conversion % | Products |
|---|---|---|---|---|---|---|
| 1 | Tetralin | 100 | 0.5 | 24.5 | 97 | octalin |
| 2 | p-xylene | 50 | 0.25 | 24 | 94 | 1,4-dimethylcyclohexene |
| 3 | 1-naphthol | 25 | 0.125 | 24 | 90–95 | 5,6,7,8-tetrahydro-1-naphthol |
| 4 | 2-naphthol | 25 | 0.25 | 24 | 90–95 | 2-hydroxy-$\Delta^{9,10}$-octalin, $\Delta^{9,10}$-octalin |
| 5 | 1-methylnaphthalene | 25 | 0.25 | 24 | 90–95 | 1-methyl-$\Delta^{9,10}$-octalin |
| 6 | 2-methylnaphthalene | 25 | 0.25 | 24 | 90–95 | 2-methyl-$\Delta^{9,10}$-octalin |
| 7 | 1,2-diphenylethane | 25 | 0.25 | 24 | 90–95 | 1,2-bis(1-cyclohexenyl)ethane |
| 8 | diphenylmethane | 25 | 0.25 | 25 | 90–95 | bis(1-cyclohexenyl)methane |
| 9 | 1-methoxynaphthalene | 25 | 0.25 | 24 | 90–95 | 5,6,7,8-tetrahydro-1-naphthol, $\Delta^{9,10}$-octalin, $\Delta^{1,9}$-octalin, $\alpha$-decalone |
| 10 | 2-methoxynaphthalene | 25 | 0.25 | 26.5 | 90–95 | 2-hydroxy-$\Delta^{9,10}$-octalin, $\Delta^{9,10}$-octalin, $\Delta^{1,9}$-octalin |
| 11 | 1-naphthylamine | 25 | 0.25 | 17 | 90–95 | 5,6,7,8-tetrahydro-1-naphthylamine |

The following general work-up procedure was utilized to recover the olefin products. The reaction vessel was cooled to 0° C. and either diethyl ether or n-pentane was added. The material was then hydrolyzed by the careful addition of aqueous HCl suitably having a concentration between 2M and 3M, thereby dissolving the calcium salts completely. The layers were separated and the aqueous layer was extracted with two portions of diethyl ether or n-pentane. The extracts were combined with the organic phase from the reaction mixture, then washed with two portions of water, two portions of 5% HCl, one portion of 5% NaHCO$_3$, and one portion of brine, and then dried over anhydrous Na$_2$SO$_4$. The solvent was removed either by rotary evaporation or fractional distillation depending on the volatility of the product. In some cases reduced pressure was necessary to remove the last traces of solvent.

The results of tests on eleven starting materials are summarized in Table 1. The percent conversion was quite high, ranging from about 90% to about 100% of theory.

In a separate but related embodiment of the process of the present invention, one or more soluble salts are added to the reaction mixture for the purpose of maintaining the alkylene polyamine in solution at low temperatures. For this purpose, the sodium and calcium halides are especially suitable, such as sodium bromide or calcium chloride, and are satisfactorily used in a weight ratio to the alkylene polyamine between about 0.5:1 and about 1.5:1. Other salts include sodium chloride, sodium iodide, calcium fluoride, calcium bromide, and the like. Salts of other metals of the alkali-metal and alkaline-earth-metal groups may also be used, but are less attractive for economic reasons.

While we have described the invention with reference to certain specific starting materials, operating conditions, and procedures, it is to be understood that such matters are intended to be illustrative only and not by way of limitation. Numerous modifications and eguivalents will be apparent to those of ordinary skill in this art without departing from the spirit of the invention.

What is claimed is:

1. A method for reducing an organic compound having at least one benzene ring and obtaining therefrom a cyclic olefin having the same structure as such organic compound except for degree of unsaturation, which comprises contacting such organic compound with a reaction mixture comprising ethylenediamine and calcium metal at a temperature between about −10° C. and about 100° C., for a period of time sufficient to effect the said reduction, the proportion of calcium metal to such organic compound being at least about 10% in excess of the stoiohiometric quantity necessary for complete reduction of such benzene ring, the said reaction medium also including, when the excess of calcium is less than 100%, an inert abrasive particulate substance, whereby a cyclic olefin is obtained having at least one double bond and having a second double bond when the benzene ring bears a substituent hindering the said reduction.

2. The method of claim 1 wherein such organic compound has less than four substituents on the said benzene ring and is reduced to a monoolefin of cyclic structure corresponding to such organic compound except for degree of unsaturation.

3. The method of claim 2 wherein such organic compound is p-xylene.

4. The method of claim 2 wherein such organic compound is tetralin.

5. The method of claim 2 wherein such organic compound is diphenylmethane.

6. The method of claim 2 wherein such organic compound is 2-naphthol

7. The method of claim 2 wherein such organic compound is 1-methylnaphthalene.

8. The method of claim 2 wherein such organic compound is 2 methylnaphthalene.

9. The method of claim 2 wherein such organic compound is 1,2 diphenylethane.

10. The method of claim 2 wherein such organic compound is 1-methoxynaphthalene.

11. The method of claim 2 wherein such organic compound is 2-methoxynaphthalene.

12. The method of claim 1 wherein such organic compound is 1-naphthol and the resulting product is 5,6,7,8 tetrahydro-1-naphthol.

13. The method of claim 1 wherein such organic compound is 1-naphthylamine and the resulting product is 5,6,7,8-tetrahydro 1 naphthylamine.

14. The method of claim 1 wherein such organic compound has four substituents on the benzene ring and is reduced to a diolefin of corresponding cyclic structure.

15. The method of claim 14 wherein such organic compound is durene.

16. The method of claim 14 wherein such organic compound is anthracene.

17. The method of claim 1 wherein the proportion of calcium metal to such organic compound is at least 100% in excess of the stoichiometric quantity necessary for complete reduction of such benzene ring.

18. The method of claim 1 wherein such organic compound is contacted with calcium metal, ethylenediamine, and sand, the proportion of calcium metal to such organic compound being less than 100% of the stoichiometric quantity necessary for complete reduction of such benzene ring.

* * * * *